United States Patent [19]

Dominique et al.

[11] Patent Number: 4,659,179
[45] Date of Patent: Apr. 21, 1987

[54] JIG FOR INSCRIBING A SUBSTRATE

[75] Inventors: Harry P. Dominique; Clinton A. Waggoner, both of Victoria, Canada

[73] Assignee: Her Majesty the Queen in right of Canada, as represented by the Minister of National Defence of Her Majesty's Canadian Government, Ottawa, Canada

[21] Appl. No.: 788,220

[22] Filed: Oct. 16, 1985

Related U.S. Application Data

[63] Continuation-in-part of Ser. No. 716,612, Mar. 28, 1985, abandoned, which is a continuation of Ser. No. 418,840, Sep. 16, 1982, abandoned.

[30] Foreign Application Priority Data

Nov. 18, 1981 [CA] Canada .................................. 390369

[51] Int. Cl.⁴ .......................... G02B 00/00; A61B 5/08
[52] U.S. Cl. ....................................... 350/320; 33/562
[58] Field of Search ....................... 350/534, 536, 320; 33/562

[56] References Cited

U.S. PATENT DOCUMENTS 3,104,467  9/1963  Lloyd-Young .
3,565,537  2/1971  Fielding ............................. 350/535
3,813,787  6/1974  Mercorelli .

Primary Examiner—John K. Corbin
Assistant Examiner—Vincent J. Lemmo
Attorney, Agent, or Firm—Nixon & Vanderhye

[57] ABSTRACT

The invention disclosed is a jig to facilitate the inscription of a pattern on a substrate, typically a glass microscope slide. The jig includes means for positioning the substrate and template means overlying the substrate. The pattern is preferably u-shaped to define a liquid flow channel along the long dimension of the slide for use of the inscribed slide in ferrography.

7 Claims, 6 Drawing Figures

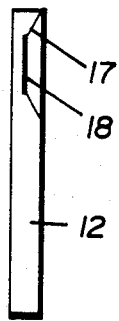
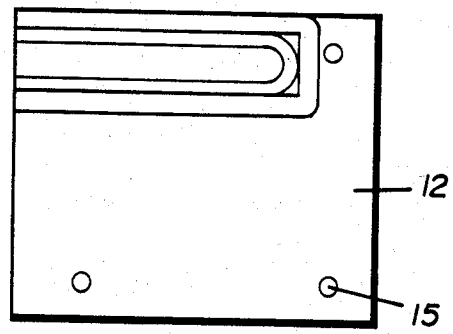
FIG. 4  FIG. 3
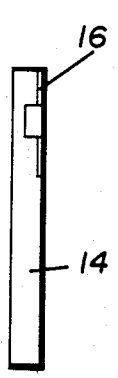
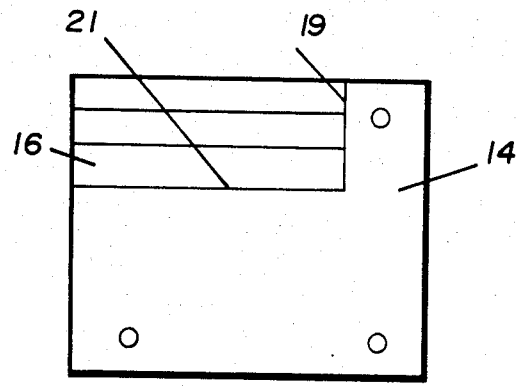
FIG. 6  FIG. 5

JIG FOR INSCRIBING A SUBSTRATE

This application is a continuation-in-part of application Ser. No. 716,612 filed Mar. 28, 1985 which is a continuation of application Ser. No. 418,840 filed Sept. 16, 1982, both now abandoned.

This invention relates to the optical analysis by microscope of hyperfine particulate materials deposited on a substrate from a liquid medium, and in particular to a jig to facilitate inscription of a pattern on the substrate.

BACKGROUND OF THE INVENTION

The use of magnetic techniques for separating ferromagnetic materials from background substances has been known for quite some time. Recent refinements of such techniques have made it possible to precipitate hyperfine ferromagnetic wear particles from a lubricant sample taken from a machine, such as a diesel engine, and to determine the wear condition of the machine by optical analysis of such particles. A detailed description of apparatus and procedures for performing such precipitation and analysis is set forth in U.S. Pat. No. 4,047,814, issued on Sept. 13, 1977 to Vernon C. Westcott. Specifically, a lubricant sample is flowed along a shallow channel in an inclined glass substrate positioned over a magnet, the air-gap of which is aligned with the longitudinal axis of the substrate. Ferromagnetic wear particles are drawn by magnetic force down from the lubricant liquid so as to deposit onto the substrate surface. The substrate is typically in the form of a thin rectangular glass slide, provided with a pair of spaced parallel Teflon ® strips secured to the edges of the slide to define a central liquid flow channel along the dimension of the slide. In carrying out this procedure with ferromagnetic wear particles, the larger particles are precipitated first, and the smaller particles are precipitated further along the flow path. Analysis, for example, by microscope, of the relative proportions of large and small size wear particles provides significant information about the state of wear of the machine from which the lubricant sample was taken.

SUMMARY OF THE INVENTION

According to the invention, a jig for use in inscribing a substrate is contemplated, comprising means for positioning said substrate; and template means overlying said substrate such that the outline of said template means may be inscribed upon said substrate.

A method of preparing a sample containing hyperfine particulate materials for optical microscopic analysis is also provided.

BRIEF DESCRIPTION OF THE DRAWING

In the drawing which illustrates a preferred embodiment of the invention,

FIG. 3 is a plan view of the top plate of the jig according to the invention;

FIG. 4 is a side elevation of the top plate of the jig according to the invention;

FIG. 5 is a plan view of the bottom plate of the jig according to the invention; and FIG. 6 is a side elevation of the bottom plate of the jig according to the invention.

DESCRIPTION OF A PREFERRED EMBODIMENT

Figure 1:
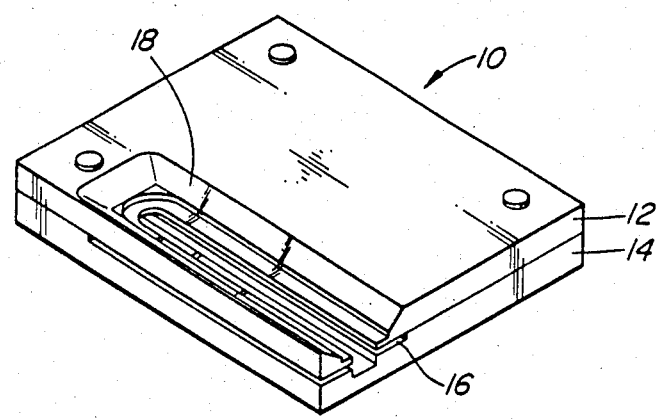
FIG. 1 is a perspective view of the jig according to the invention.
Figure 2:
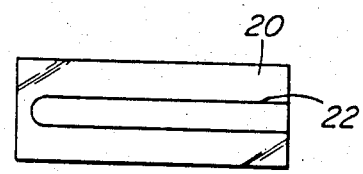
FIG. 2 is an illustration of a substrate inscribed in the jig according to the invention.

Referring to the drawing a jig 10 for use in inscribing a substrate is illustrated. The jig comprises a pair of mating rectangular metal (aluminum) plates 12 and 14, conveniently held together by mechanical fasteners 15.

The bottom plate 14 is provided with a groove 16 machined therein at one corner of the top surface of the plate, to the size of a (60 mm×24 mm) microscope cover glass (#2 thickness-0.010 inches). As seen in FIG. 5, the groove 16 terminates in stop surfaces 19 and 21. The bottom plate thus serves as positioning means for a translucent substrate which is in the form of a glass microscope slide.

The top plate 12 includes a u-shaped opening 18 machined therein which aligns with the groove 16 when the plates are mated. Thus, when a slide 20 is positioned in groove 16, top plate 12 provides template means overlying the slide 20 to provide for the inscription of the outline of the u-shaped opening 18 on the slide. The edges of the plate adjacent the u-shaped opening 18 taper outwardly at 17 to provide sufficient relief to accommodate a scribing instrument.

The slide 20 may thus be loaded and unloaded from the jig 10 via groove 16 without separating the top plate 12 from the bottom plate 14.

In operation, a slide 20 is inserted between the plates into corner groove 16 and held firmly against stop surfaces 19 and 21 with the users left hand while a u-shaped inscription 22, defined by a pair of spaced parallel lines including a liquid-flow channel therebetween, is inscribed by a scribing instrument held in the user's right hand. A technical pen filled with a suitable oil-retardant material such as Nyebar ® has been found appropriate. A Mars ® type 700-030 or 700-035 pen may be conveniently employed. Nyebar ® includes solvent which evaporates upon drying, leaving a polymer film which provides an oil-retardant barrier. A contaminated liquid sample is then flowed along the long dimension of the slide in the channel toward the free ends of the u. The bridge of the u prevents any tendency for the liquid sample to flow back, although the slide is inclined in use to minimize this possibility.

It will be appreciated by those skilled in the art that a two-piece jig is used to facilitate machining and that materials other than aluminum which are susceptible to machining may also be employed. Furthermore, the substrate need not be of glass. In fact, opaque substrates such as aluminum may be employed for qualitative and quantitative optical or electron microscope analysis of the sample. It will also be appreciated that designs other than that described above may be inscribed upon the substrate by changing the pattern of the template means. For example, in biological work it might be desirable to inscribe a series of circles on a substrate to certain drops of solution for microbial counting.

The embodiments of the invention in which an exclusive property or privilige is claimed are defined as follows:

1. A jig to facilitate inscription of a pattern on a substrate, said jig comprising a pair of mating plates held together by fastening means, a bottom plate having a groove at one corner of its top surface for positioning and maintaining the position of said substrate during inscription of the pattern on said substrate, and a top plate including a shaped opening which aligns with said groove when the plates are mated to provide a template for the inscription of said pattern on said substrate, wherein said groove provides a substrate-receiving spacing between said top and bottom plates at said corner to facilitate loading and unloading of said substrate without separating said top and bottom plates.

2. A jig according to claim 1, wherein the top plate includes outwardly tapering edges adjacent the shaped opening.

3. A jig according to claim 2, wherein said groove in said bottom plate terminates in a stop surface for said slide.

4. A jig according to claim 3, wherein the opening in said top plate is u-shaped.

5. A jig according to claim 4, wherein the substrate is a thin, rectangular glass microscope slide.

6. A method of preparing a sample containing hyperfine particulate materials for optical microscope analysis, including the steps of:
   (a) positioning a rectangular microscope slide in
       a jig comprising a pair of mating plates held together by fastening means;
       a bottom plate having a groove at one corner of its top surface for receiving said rectangular microscope slide and terminating in a stop surface for said slide whithin said groove, wherein said groove positions and maintains the position of said slide during inscription of a u-shaped pattern onto said slide; and
       a top plate having a u-shaped opening aligned with and smaller than said groove overlying said microscope slide to guide a scribing instrument to inscribe said shaped pattern on said slide.
   (b) inscribing a u-shaped pattern having a pair of spaced parallel lines on said microscope slide to define a liquid-flow channel therebetween by placing a scribing instrument in said u-shaped opening and tracing said opening as a template with said scribing instrument; and
   (c) applying a contaminated liquid sample to the thus-inscribed u-shaped pattern and flowing said sample along the long dimension of the slide towards the free ends of the u, the bridge of the u-shaped pattern preventing any tendency for the liquid to flow back.

7. The method according to claim 6 in which the inscribed u-shaped pattern is an oil resistant polymer film barrier.

* * * * *